United States Patent
Suman

(10) Patent No.: US 9,682,086 B2
(45) Date of Patent: Jun. 20, 2017

(54) MOLYBDENUM COMPOUNDS FOR USE IN THE TREATMENT OF CYANIDE POISONING

(71) Applicants: Háskóli Íslands, Reykjavik (IS); Sigríður Guðrún Suman, Kópavogur (IS)

(72) Inventor: Sigrður Guðrún Suman, Kópavogur (IS)

(73) Assignees: Háskóli Íslands, Reykjavik (IS); Sigríður Guðrún Suman, Kópavogur (IS)

( * ) Notice: Subject to any disclaimer, the term of this patent is extended or adjusted under 35 U.S.C. 154(b) by 0 days.

(21) Appl. No.: 15/023,181

(22) PCT Filed: Sep. 25, 2014

(86) PCT No.: PCT/EP2014/070559
§ 371 (c)(1),
(2) Date: Mar. 18, 2016

(87) PCT Pub. No.: WO2015/044304
PCT Pub. Date: Apr. 2, 2015

(65) Prior Publication Data
US 2016/0206625 A1    Jul. 21, 2016

(30) Foreign Application Priority Data
Sep. 25, 2013    (IS) .............................. 9035

(51) Int. Cl.
*A61K 31/555*  (2006.01)
*C07F 11/00*  (2006.01)
*A61K 33/04*  (2006.01)
*C07C 211/05*  (2006.01)
*C07F 17/00*  (2006.01)

(52) U.S. Cl.
CPC ............. *A61K 31/555* (2013.01); *A61K 33/04* (2013.01); *C07C 211/05* (2013.01); *C07F 11/005* (2013.01); *C07F 17/00* (2013.01)

(58) Field of Classification Search
CPC ...... A61K 31/555; A61K 33/04; C07F 11/005
See application file for complete search history.

(56) References Cited

PUBLICATIONS

Snaebjornsson et al. ,Icelandic Chemical Society, 2013, 1 page.*
Suman et al., ACS abstracts, 2011, 1 page.*
Brenner, Matthew et al., "Intramuscular Cobinamide Sulfite in a Rabbit Model of Sublethal Cyanide Toxicity" Annals of Emergency Medicine, Apr. 2010, pp. 352-363, vol. 55, No. 4.
Coucouvanis, D. et al., "Reactivity of the Mo(O)(S) Functional Group in the [(L)Mo(O)(µ-S)$_2$Mo(O)(S)]$^{n-}$ Dimeric Thiomolybdate Complexes (L=C$_5$H$_5^-$, n=1; S$_4^{2-}$, n=2) and Implications Regarding the Function of Xanthine Oxidase. Synthesis and Structural Characterization of [(DMF)$_3$Mo(O)(µ-S)$_2$Mo(O)(S$_2$)], [Ph$_4$P][C$_5$H$_5$)Mo(O)(µ-S)$_2$Mo(O)(S$_2$)], [Ph$_4$P]$_2$[(S$_4$)Mo(O)(µ-S)$_2$Mo(O)(S)], and (Et$_4$N)$_4$\{[(S$_4$)Mo(O)(µ-S)$_2$Mo(O)(S)]$_2$\}" J. Am. Chem. Soc., 1991, pp. 5271-5282, vol. 113.
Ivankovich, Anthony D. et al., "Cyanide Antidotes and Methods of Their Administration in Dogs: A Comparative Study" Anesthesiology, 1980, pp. 210-216, vol. 52.
Suman, Sigridur "Inor 774—Molybdenum-sulfur catalyst for cyanide poisoning" Mar. 29, 2011, XP-002732940.
Publications and Patents—Sigríður Suman, Associate Professor, pp. 1 and 2, XP-002732871.
International Search Report for PCT/EP2014/070559 dated Dec. 12, 2014.

* cited by examiner

*Primary Examiner* — Kyle Purdy
(74) *Attorney, Agent, or Firm* — Knobbe Martens Olson & Bear LLP

(57) ABSTRACT

The present invention relates to compositions comprising molybdenum compounds, novel molybdenum compounds, kits and methods for their preparation. In particular, the present invention relates to compositions comprising molybdenum compounds for use in the treatment of cyanide poisoning in mammals, in particular humans.

31 Claims, 7 Drawing Sheets

MOLYBDENUM COMPOUNDS FOR USE IN THE TREATMENT OF CYANIDE POISONING

CROSS REFERENCE TO RELATED APPLICATIONS

This application is a U.S. National Phase Application of PCT International Application Number PCT/EP2014/070559, filed on Sep. 25, 2014, designating the United States of America and published in the English language, which is an International Application of and claims the benefit of priority to Icelandic Patent Application No. 9035, filed on Sep. 25, 2013. The disclosures of the above-referenced applications are hereby expressly incorporated by reference in their entireties.

TECHNICAL FIELD OF THE INVENTION

The present invention relates to compositions comprising molybdenum compounds, novel molybdenum compounds, kits and methods for their preparation. In particular, the present invention relates to compositions comprising molybdenum compounds for use in the treatment of cyanide poisoning in mammals, in particular humans.

BACKGROUND OF THE INVENTION

An efficient mass treatment for cyanide poisoning due to accidental or intentional exposure is essential for public health. Cyanide poisoning is rapid and treatment options are limited, and thus the survival rate is low.

Cyanide is used industrially in tasks, such as fumigation, electroplating, and mining. It is well known in suicides, homicides, and warfare and is increasingly recognized as a toxin in building fires. It is formed in thermal combustion of nitrogen-containing polymers, which release carbon monoxide and cyanide faster than natural products such as wood (see Alarie, Y., Annu. Rev. Pharmacol. Toxicol. 25, 325-347 (1985)). Cyanide is therefore considered a common cause for inhalation injury in all uncontrolled building fires in the civilian population (see Anderson, R. A. and Harland, W. A., Med. Sci. Law 22, 35-40 (1982); and Ballantyne, B. In Clinical and Experimental Toxicology of Cyanides (B. Ballantyne and T. Marrs, Eds.), pp. 248-291 (1974); and in Clark, C. J., Campbell, D., and Reid, W. H., Lancet 1, 1332-1335. and same authors in Hum. Toxicol. 6, 139-145 (1981); and in Silverman, S. H., Purdue, G. F., Hunt, J. L., and Bost, R. O., J. Trauma 28, 171-176 (1988)).

Several international organizations, including the World Health Organization (WHO) have designated cyanide a priority chemical in relation to potential impact on human health and the environment.

Cyanide is naturally metabolized in the liver by cysteine 247 in the rhodanase enzyme active site. The rhodanase is activated by donation of sulfur from the sulfane pool to form cysteine perthiol, (—SSH), which reacts instantaneously with cyanide to form nontoxic thiocyanate. Natural substrates for cyanide metabolism become depleted rapidly when cyanide exposure is high. Cyanide is a specific inhibitor of cytochrome c oxidase, resulting in histotoxic hypoxia, followed by lactic acidosis as a consequence of anaerobic cell (see Steven J. Baskin, and Thomas G. Brewer, "Cyanide Poisoning," "Medical Aspects of Chemical and Biological Warfare," (Frederick R. Sidell, COL Ernest T. Takafuji, and COL David R. Franz, Eds.) and "Textbook of Military Medicine: Medical Aspects of Chemical and Biological Warfare", (BG Russ Zajtchuk and COL Ronald F. Bellamy, Eds.), Office of the Surgeon General, Walter Reed Army Medical Center, Washington, D.C. (1997)).

A lethal blood concentration of cyanide has been found to depend on exposure level and amount of oxygen in the blood. For example, oxygen deprivation due to concurrent carbon monoxide inhalation at high levels increases the $LT_{50}$ tenfold (see see Alarie, Y., Annu. Rev. Pharmacol. Toxicol. 25, 325-347 (1985)).

A lethal cyanide dose can be a large range: from 1.0 to 6.0 mg/L (40 to 200 µM). Half-life of cyanide at toxic levels, where blood tests were obtained in the ambulance shortly after exposure (see S. W. Borron, B. Mégarbane., F. J. Baud, Case 6-2004: Severe Burns from a Nightclub Fire. *New England Journal of Medicine* 2004, 2314.), has been determined as 1 hour, while studies showed that in nonfatal cases a half-life of 3 h was determined (see Barillo, D. J., J. Burn Care Rehabil., 15, 46-57 (1994); Kratz, A., Ferraro, M., Sluss, P., Lewandowski, K. B., Laboratory Reference Values. N. Engl. J. Med., 351, 1548-1563 (2004)). Lower-level inhalation exposure or oral ingestion has a survival time of about 30 min (see). Biological detoxification of cyanide from the human body takes place through a variety of minor pathways (see [1]Keilin, D., Proc R Soc Lond [Biol] 106:418-444 (1930); Isom, G. E. and Way J. L., Toxicol. Appl. Pharmacol. 74:57-62 (1984)).

The rate of natural detoxification of cyanide by the rhodanese enzyme has been measured as 0.017 mg/kg*min (see McNamara, B. P., Estimation of the toxicity of hydrocyanid acid vapors in man. (Edgewood Arsenal Technical Report No. EB-TR-76023, Army Department (1976)). Because of the rapidly progressive nature of cyanide toxicity, treatment is ideally administered shortly after exposure. Antidotes and treatments are often administered with oxygen, or thiosulfate.

Conventional approaches for treating cyanide poisoning may be organized into the following groups:

Methemoglobin Inducers.

This group counts amyl and sodium nitrites, and DMAP or 4-dimethylaminophenol. Nitrites oxidize hemoglobin to methemoglobin, which has higher affinity for cyanide than for oxygen. Methemoglobin chelates cyanide to form cyanomethemoglobin at the cost of oxygen-carrying capacity and is known to cause hypotension (see Hall and Kulig 1989). Carboxyhemoglobin formed upon inhalation of carbon monoxide causes oxygen deprivation, and using methemoglobin formers to treat cyanide poisoning concurrently has been shown to increase victim fatality (see Moore, S. J., Norris, J. C., Walsh, D. A., Hume, A. S., The Journal of Pharmacology and Experimental Therapeutics, 242(1), 70-74, (1987)). DMAP or 4-dimethylaminophenol is used only for severe cyanide poisoning because it involves significantly increased risk of oxygen deprivation or anoxia (see Baskin and Brewer), and unsuitable for treatment of fire victims. Nitrites in combination with thiosulfate have been the most used treatments in USA.

Chelators.

This group counts vitamin B12 derivatives, and EDTA. Hydroxocobalamin (vitamin $B_{12}$) is a cyanide chelator without significant side effects. Hydroxocobalamin was approved for use in Cyanokit™ (Merck Sante s.a.s.) by Food and Drug Administration (FDA) in USA in December 2006. The doses required for treatment are in the range of 5 to 20 g per patient. Adverse event reports include skin discoloration from pink to red and red-colored urine, which resolves over a few days (see S. W. Borron, F. J. Baud, B. Mégarbane, C. Bismuth, Am. J. Emer. Med., 25, 551-558, (2007)). The compound is nontoxic and has been used widely in Europe. The drawbacks include a short shelf life and light sensitivity, and a costly dose. It is unsuitable for mass treatment. Dicobalt edetate (cobalt EDTA or Kelocyanor) is more effective than the combination of sodium nitrite and sodium thiosulfate, but severe toxicity of cobalt in the absence of cyanide is a deterrent to using treatments like cobalt EDTA without solid proof of cyanide intoxication. Cobinamide has progressed towards clinical trials (see Brenner, M., Kim, J. G., Lee, J., Mahon, S. B., Lemor, D., Ahdout, R., Boss, G. R., Blackledge, W., Jann, L., Nagasawa, H. T., Toxicol Appl Pharmacol, 248:269-276 (2010)). It is a highly soluble vitamin $B_{12}$ precursor and has higher efficacy than Cyanokit™. It reacts stoichiometrically with cyanide.

Other Treatments.

This group counts thiosulfate, and a mercaptopyruvate prodrug. Thiosulfate has been used off-label for a long time. It is now in the process of FDA approval. It reacts with cyanide as it is slowly released from cyanomethemoglobin, forming thiocyanate. Thiosulfate treatment requires intravenous administration of large quantities (see Ivankovich, A. D., Braverman, B., Kanuru, R. P., Heyman, H. J., and Paulissian, R., Anesthesiology, 52, 210-216 (1980) or ~12 g/10 min as is the current standard. Additionally, thiosulfate is commonly administered with other treatments to facilitate thiocyanate formation since it does not affect oxygen carrying capacity in fire victims. The reaction rate of thiosulfate with cyanide is too slow to save lives by itself. Mercaptopyruvate prodrug or sulfanegen, is recent development and appears safe, and moderately effective. It is administered intravenously, where β-mercapto-pyruvate sulfur-transferase transforms it into the active drug. The downside is that it is rather unstable (Brenner, M., Kim, J. G., Mahon, S. B., Lee, J., Kreuter, K. A., Blackledge, W., Mukai, D., Patterson, S., Mohammad, O., Sharma, V. S., Boss, G., Ann. Emerg. Med., 55:32-362 (2009)).

The treatments known in the art as described above have in common either a requirement for a large quantity of treatment, risk of toxicity, or a requirement for IV administration.

Accordingly, there is a need for a new cyanide poisoning treatment that requires only a small dose of nontoxic compounds suitable for treatment of several victims suffering from smoke inhalation or industrial accidents.

SUMMARY OF THE INVENTION

Thus, it is an object of the present invention to provide novel compounds, compositions and kits for use in the treatment of cyanide poisoning, which only requires a small dose of nontoxic compounds that solves the above mentioned problems of the prior art.

Thus, one aspect of the invention relates to a novel molybdenum compound according to the following formula

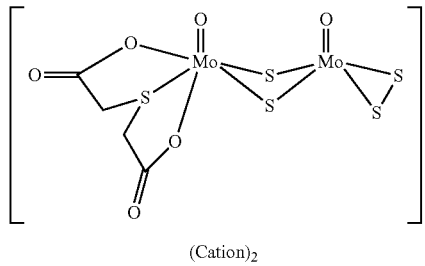

(Cation)$_2$ and, in particular, its use in the treatment of cyanide poisoning in a mammal, preferably a human.

Another aspect of the present invention relates to a composition comprising a molybdenum compound according to the following formula,

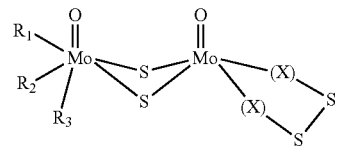

Wherein
X is S or a bond; and
$R_1$, $R_2$, and $R_3$ independently or together are one or more of the ligands selected from the group consisting of: a mono- or disaccharide having 3 to 12 carbon atoms, a natural amino acid, a primary, secondary, or tertiary amine, substituted with an alkyl having 1 to 5 carbon atoms, a mono- or di-carboxylic acid having 1 to 5 carbon atoms, which may be substituted with O, S, $CH_3S$— or N, a thiocarboxylic or dicarboxylic acid having 1 to 5 carbon atoms, a primary, secondary or tertiary amide having 1 to 5 carbon atoms, wherein the side chains attached to the nitrogen is an alkyl having 1 to 5 carbon atoms, a complexing agent, such as EDTA, cyanide, thiocyanate ($SCN^-$), sulfite, disulfide or tetrasulfide, and wherein $R_3$ may be an electron pair;
for use in the treatment of cyanide poisoning in a mammal.

In a further aspect, the present invention provides a kit comprising a compound or a composition according to the present invention for use in the treatment of cyanide poisoning.

Yet another aspect of the present invention is to provide a process for preparing the novel molybdenum compound according to the present invention, comprising:
1) suspension of a molybdenum compound having the following formula

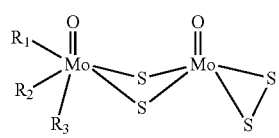

Wherein $R_1$, $R_2$, and $R_3$ independently or together are one or more of the ligands selected from the group consisting of: a mono- or disaccharide having 3 to 12 carbon atoms, a natural amino acid, a primary, secondary, or tertiary amine, substituted with an alkyl having 1 to 5 carbon atoms, a mono- or di-carboxylic acid having 1 to 5 carbon atoms, which may be substituted with O, S, $CH_3S$— or N, a thiocarboxylic having 1 to 5 carbon atoms, a primary, secondary or tertiary amide having 1 to 5 carbon atoms, wherein the side chains attached to the nitrogen is an alkyl having 1 to 5 carbon atoms, a complexing agent, such as EDTA, cyanide, thiocyanate ($SCN^-$), sulfite or tetrasulfide, and wherein $R_3$ may be an electron pair;
in an inert solvent under an inert atmosphere;
2) addition of thiodiacetic acid in the presence of a base in a dry inert solvent under inert atmosphere and stirring the reaction mixture;
3) evaporation of the solvent and precipitation;

4) wash of precipitate with ethanol and ether, and optionally re-crystallisation; and
5) providing the novel molybdenum compound according to the following formula

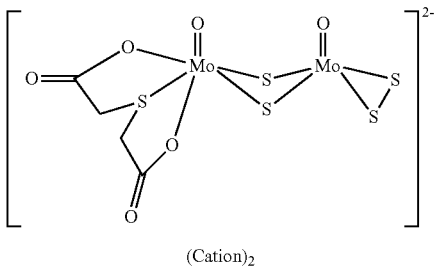

(Cation)$_2$

The catalyst used for this data collection was the compound [Mo$_2$O$_2$S$_4$(DMF)$_3$]. The compound reacts instantaneously with cyanide and forms one thiocyanate. It can be seen that thiocyanate is formed from almost all of the cyanide in the solution (83% total).

Figure 2:
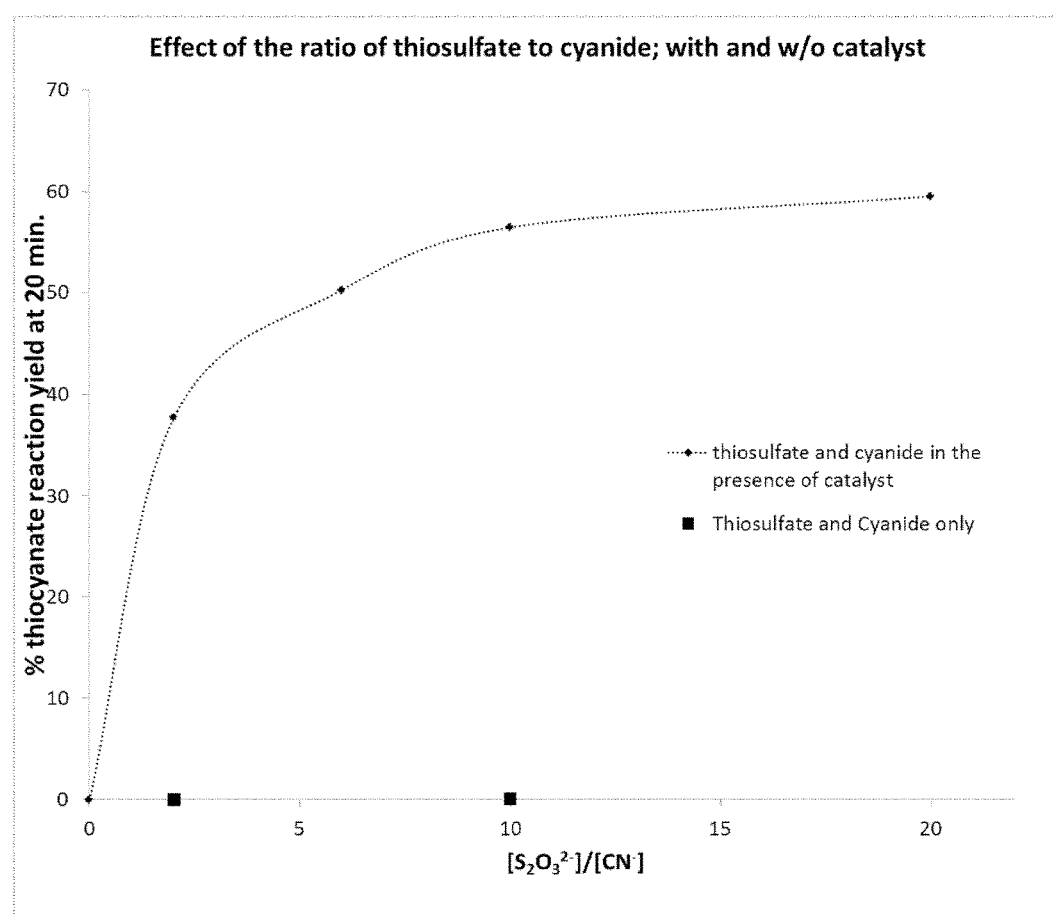

FIG. 2 shows the thiocyanate reaction yields as a function of the ratio of thiosulfate to cyanide. The line is drawn for illustration purposes.

The data is collected after 20 minutes reaction time. The catalyst amount is 10 mol % [Mo$_2$O$_2$S$_4$(DMF)$_3$] in all experiments, except for the one labelled thiosulfate and cyanide only. Thiosulfate concentration affects the amount of thiocyanate formed and it is beneficial to use more than a stoichiometric amount of thiosulfate. Excess between 3 and 10 fold shows incremental increase in thiocyanate formation. However, the largest effect is clearly in relation to the catalytic reaction with the molybdenum compound as catalyst. Thus, the reaction of cyanide and thiosulfate does not produce significant amount of thiocyanate in 20 minutes without the catalyst as compared to the reaction with the catalyst.

Figure 3:
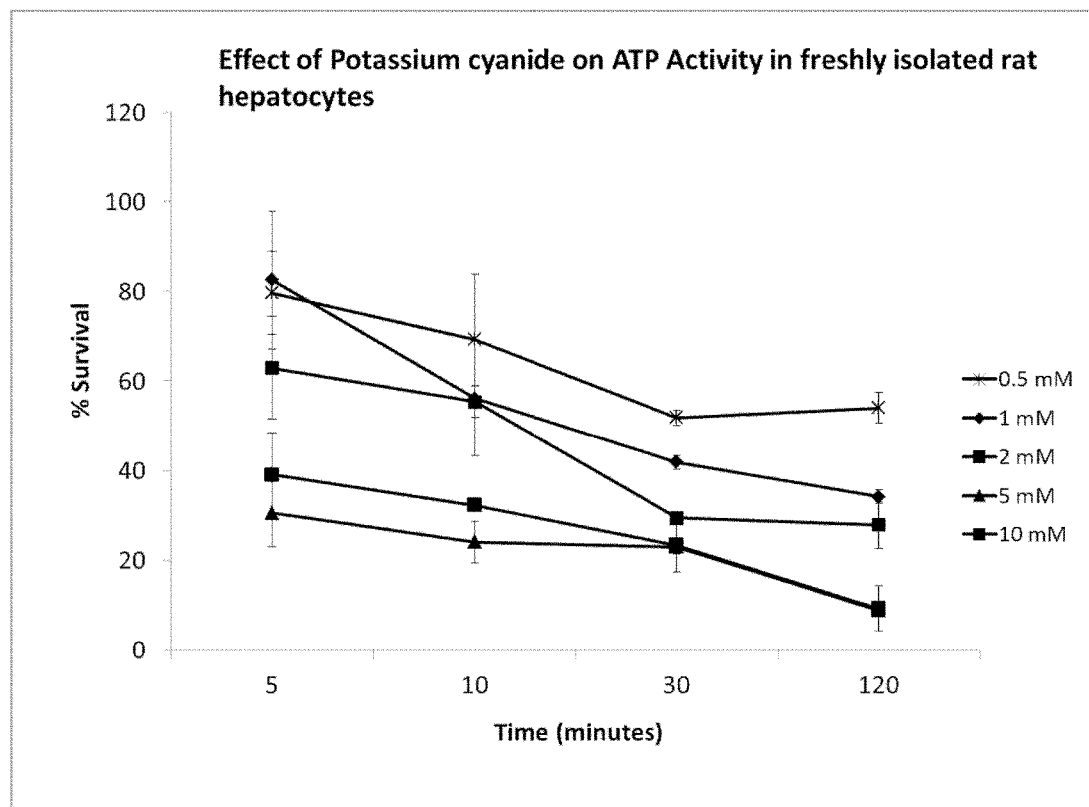

FIG. 3 shows the effect of potassium cyanide on ATP activity, which is correlated with survival, in freshly isolated rat hepatocytes. As expected, increased concentration of KCN shows decreased % survival with time. The curves were used to determine suitable concentration for KCN in experiments with thiosulfate and compounds tested. 5 mM and 10 mM have very low survival rate after 2 hours, and 2 mM concentration shows a rapidly falling survival rate with time.

Figure 4:
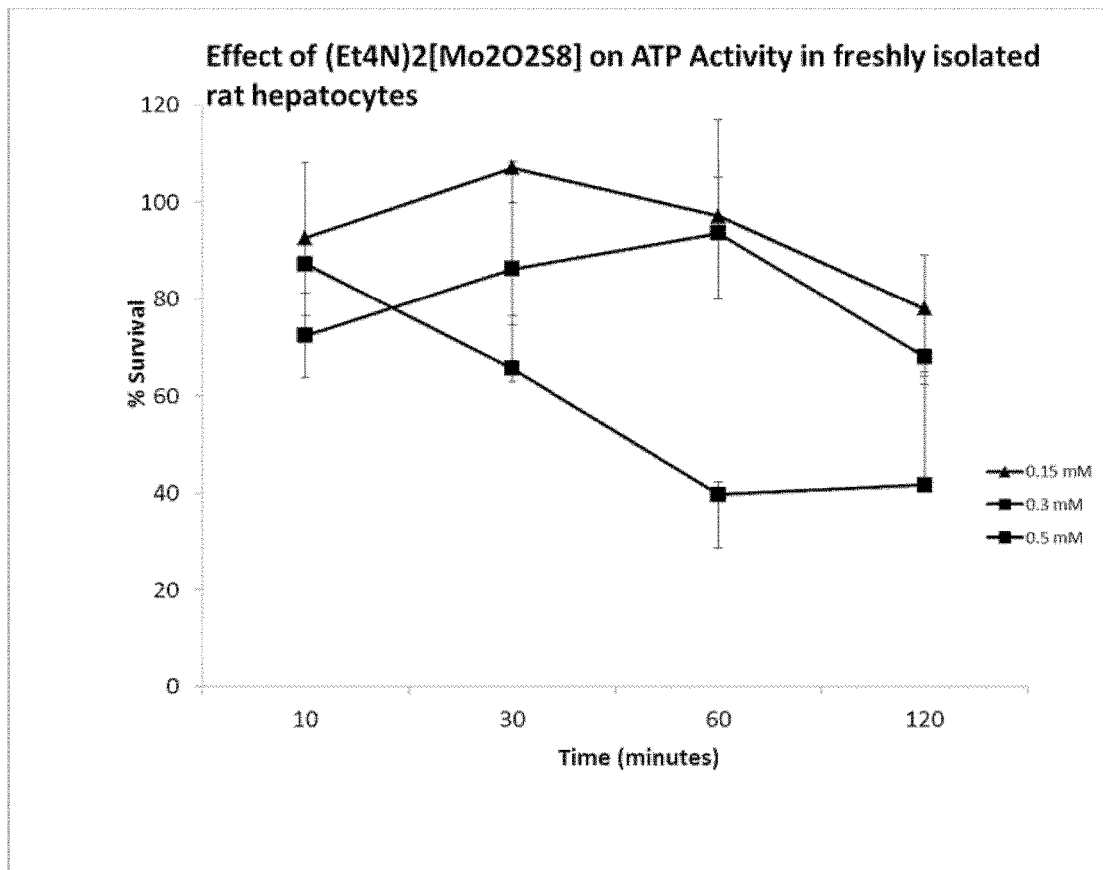

FIG. 4 shows the effect of (ET$_4$N)$_2$[Mo$_2$O$_2$S$_8$] on ATP activity, which is correlated with survival, in freshly isolated rat hepatocytes. Although molybdenum sulfur compounds are well tolerated in humans, suitable salt selection is important as shown here. This compound is very well tolerated at lower concentrations, but at 0.5 mM concentration a rapid decrease in survival is observed. This behaviour is attributed to more apparent effects of the alkylammonium salt at elevated concentration.

Figure 5:
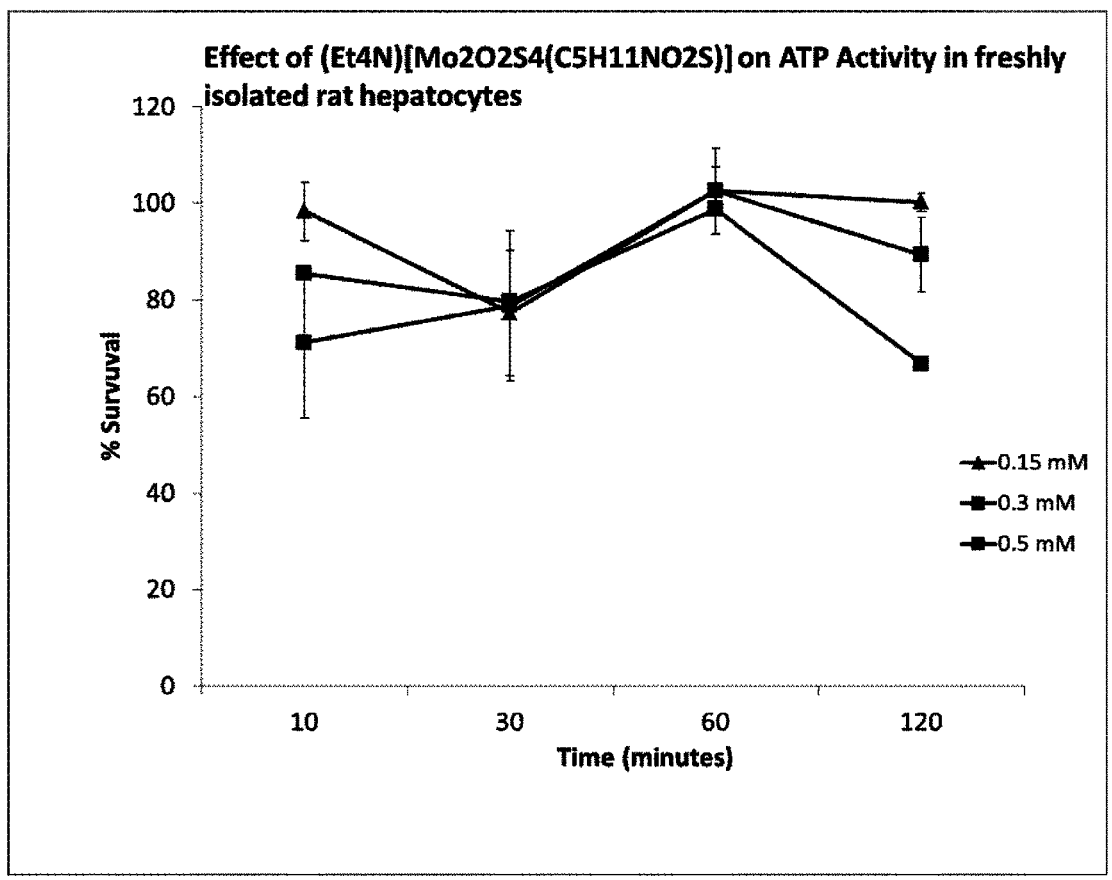

FIG. 5 shows the effect of (Et$_4$N)[Mo$_2$O$_2$S$_4$(C$_5$H$_{11}$NO$_2$S)] on ATP activity, which is correlated with survival, in freshly isolated rat hepatocytes. Here is another data set for an alkylammonium complex. Again, we believe the reduced tolerance at higher concentrations is due mainly to the alkylammonium salt, rather than to the methionine ligand (natural amino acid) of the complex.

Figure 6:
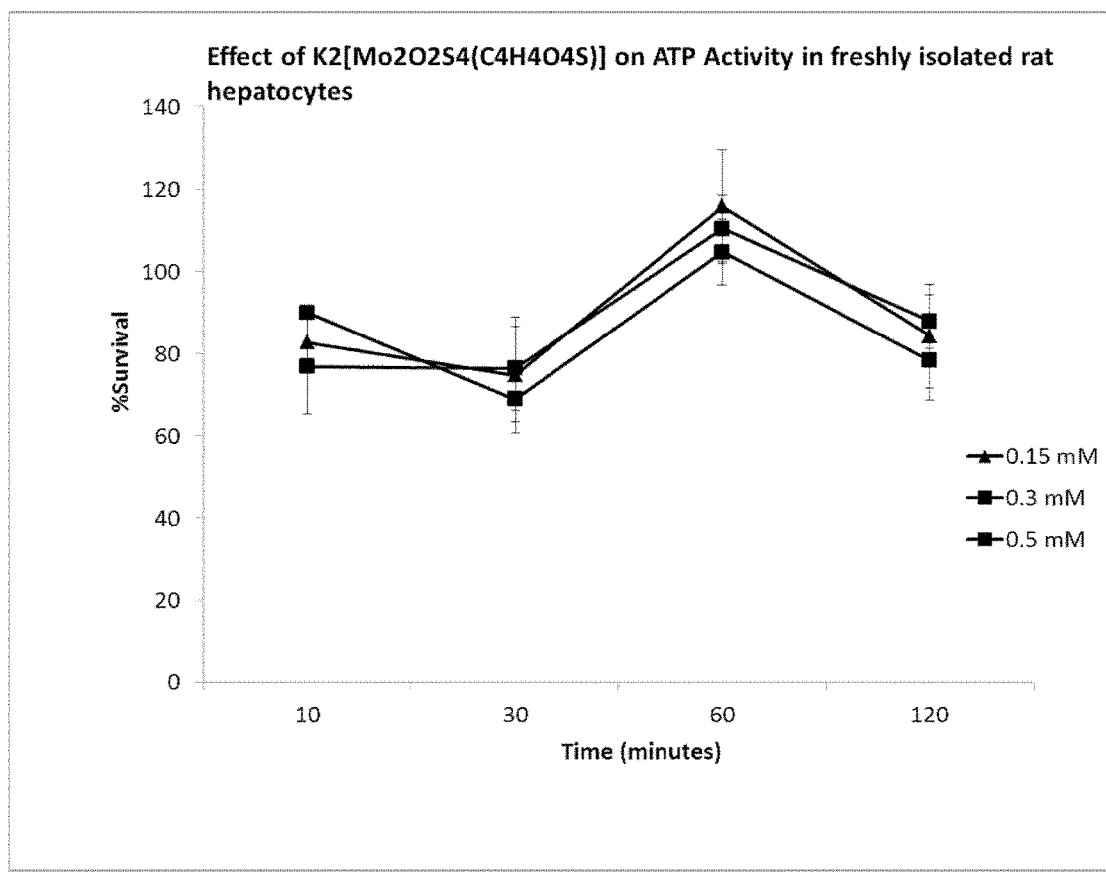

FIG. 6 shows the effect of K$_2$[Mo$_2$O$_2$S$_4$(C$_4$H$_4$O$_4$S)] on ATP activity, which is correlated with survival, in freshly isolated rat hepatocytes. A potassium salt of the thiodiacetic acid complex shows a very well tolerated compound at all of the concentrations tested. A large error bar for data at the different timepoint is due to variability of cell density between experiments (see experimental protocol).

Figure 7:
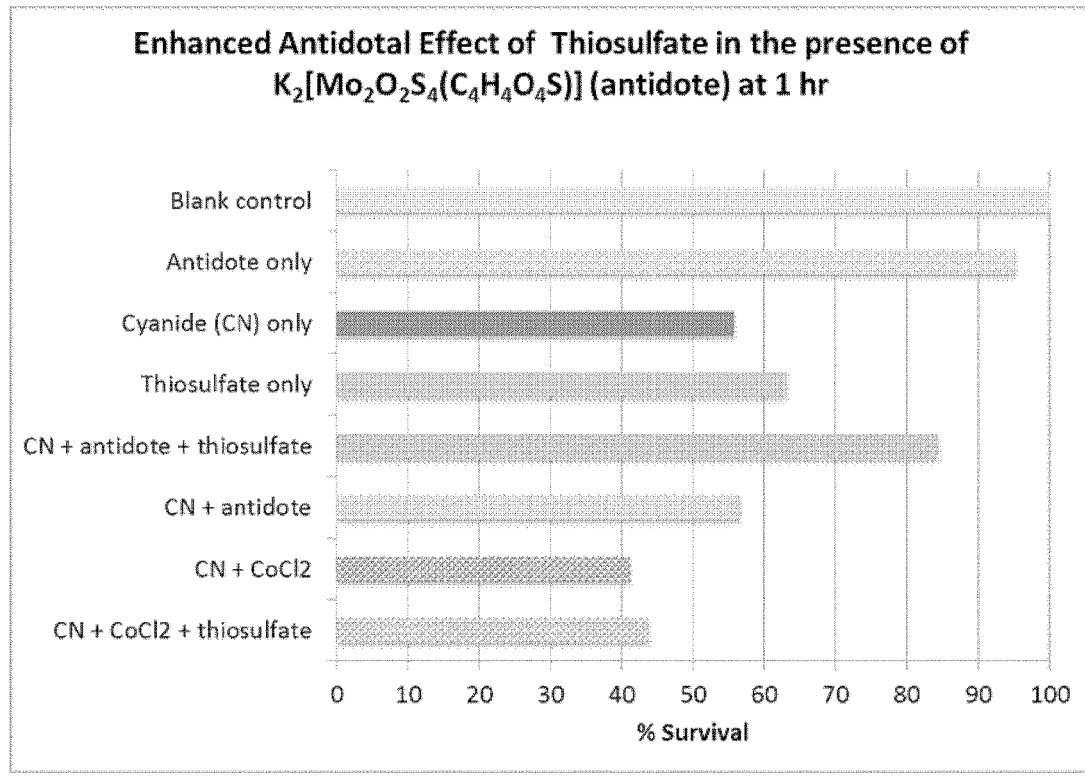

FIG. 7 shows data from toxicity and efficacy studies.

The figure shows a positive control at the top, normal growing cells as 100%. Next is the molybdenum sulfur compound, K$_2$[Mo$_2$O$_2$S$_4$(C$_4$H$_4$O$_4$S)], called "antidote". The fact that it has over 95% survival means it is non-toxic. Next is cyanide, the concentration has been adjusted such that about 50% of the cells would survive. Thiosulfate alone would seem to be less safe than the antidote. The combination of thiosulfate, cyanide and compound, clearly shows excellent survival of about 84% when combined as compared to cyanide alone or the reference compound CoCl$_2$.

Thus, the toxicity of the compound was concluded as non-toxic, and although the molybdenum compound is not very effective by itself, which is due to the fact that the compound only reacts stoichiometrically with cyanide, whereas when combined with thiosulfate it provides an excellent alternative for safe and quick administration The present invention will now be described in more detail in the following.

DETAILED DESCRIPTION OF THE INVENTION

As mentioned above, the known treatments described above have in common either a requirement for a large quantity of treatment, risk of toxicity, or a requirement for IV administration. Clearly, there is a need for a new cyanide poisoning treatment that requires only a small dose of nontoxic compounds suitable for treatment of several victims suffering from smoke inhalation or industrial accidents. The ideal delivery method is intramuscular (IM) administration because it is easier to administer to large numbers of people and to the self.

Thus, The inventor's interest in developing a cyanide poisoning treatment thinking about how to administer antidote to a large number of casualties in a short time.

Hence, a catalytic approach was believed to be most advantageous for intramuscular administration and in particular catalyzed cyanide detoxification employing a molybdenum sulfur active site using a sulfur donor, was studied.

Scheme 1

Hence, the inventors of the present invention developed a concept based on the catalytic reaction scheme shown in scheme 1 below.

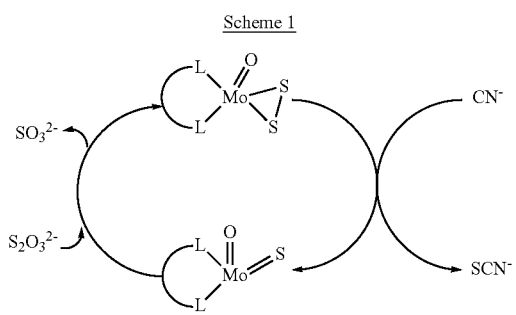

Scheme 1

-continued

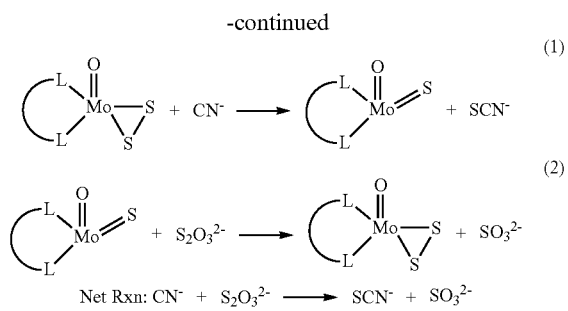

Net Rxn: $CN^- + S_2O_3^{2-} \longrightarrow SCN^- + SO_3^{2-}$

Thus, it is an object according to the present invention to provide compositions and molybdenum compounds for use in the treatment of cyanide poisoining, which minimize potential toxicity by using well-tolerated compounds with minimal quantities without sacrificing oxygen transport. In an aspect of the present invention, the cyanide detoxification treatment has two components: a Mo—S compound, and a sulfur source, such as thiosulfate. Thiosulfate has been used clinically "off label" for many years until 2012 when it was submitted to FDA for approval as a cyanide poisoning treatment.

The catalytic system can be described in two equations, the reaction of the molybdenum complex with cyanide to form thiocyanate and molybdenum sulfido (1), and the reaction of the molybdenum sulfido with a sulfur source, such as thiosulfate (2). The net reaction is the reaction of cyanide with thiosulfate to form thiocyanate and sulfite.

The present inventors have chosen to focus on suitable sulfur-bridged molybdenum dimer compounds. Without being bound by theory, the "sulfur bridge" is of interest, since it is known to facilitate sulfur atom transfers, leaving a vacant coordination site capable of accepting a new ligand without distorting the molecule geometry. The molybdenum compounds of the present invention may have the general formula; (cation)$_2$[Mo$_2$O$_2$S$_2$(S$_2$)(ligand)]. The disulfide ligand is the active site for catalysis while the second molybdenum accommodates a large variety of ligands that may coordinate in mono, bi-, or tridentate manner. The exemplary molybdenum complex compounds, (Et$_4$N)$_2$ [Mo$_2$O$_2$S$_8$] (1) to the left, and [Mo$_2$O$_2$S$_4$(DMF)$_3$] (2) to the right are shown in scheme 2 below.

Scheme 2

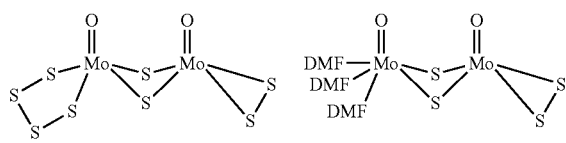

Reactions of cyanide with thiosulfate in the presence of 10% mol of complex (2) using different ratios of thiosulfate to cyanide showed that thiocyanate reaction yields increase with increased thiosulfate concentration. In FIG. 2 this is shown for 4 different ratios of thiosulfate to cyanide, and it was also shown that the reaction yield (in black squares) for the same reaction at two different ratios without complex (2).

Determination of the reaction rate for the sulfido complex was attempted using initial rates measured from reactions of (2) with cyanide at various concentrations. The present inventors discovered that thiocyanate is formed in these reactions stoichiometrically with respect to complex (2) concentration. The present inventors have verified independently that the decrease in total cyanides is due to thiocyanate formation, and that without thiosulfate only stoichiometric amount of thiocyanate is obtained. Thus, it is believed that the formation of the sulfido and thiocyanate is a rapid reaction in the catalytic thiocyanate formation observed in this system.

Studies using complex (2) as a catalyst with ratios of thiosulfate to cyanide (see FIG. 2) have shown that the thiosulfate concentration affects the amount of thiocyanate formed and it is beneficial to use more than a stoichiometric amount of thiosulfate. However, the most remarkable effect is clearly in relation to the catalytic effect of the molybdenum compound.

The combined study of efficacy and safety clearly shows that the toxicity of the molybdenum compound used was quite low, in fact non-toxic, and although the molybdenum compound is not very effective by itself, which is due to the fact that the compound only reacts stoichiometrically with cyanide, whereas when combined with thiosulfate it provides an excellent alternative for safe and quick administration (see FIG. 7).

Cyanide is a strong donor molecule when it binds to metals and as such is able to replace weaker donor ligands, even bidentate neutral ligands such as ethylenediamine (NH2CH2CH2NH2) in ligand exchange reactions of metal complexes. It is conceivable that some of the ligands employed will be replaced by cyanide under high cyanide concentrations, resulting in a dual function of the catalyst where the catalyst removes cyanide by exchanging out the ligand for two to three cyanide ligands, as well as catalytically converting the remaining cyanide to thiocyanate. The present inventors have demonstrated this reaction with a catalyst exchanging three DMF ligands and two cyanide ligands in FIG. 1B, where the catalyst removes 83% of the cyanide from solution. It was verified that the remaining 17% (±error of measurement) is cyanide bound to the molybdenum. By reacting excess cyanide with [Mo2O2S4 (DMF)3] and precipitating the product as the Et4N+ salt, we isolated crystals of a dimer (Et4N)4[Mo4O4S4(CN)4]. The sulfido moiety formed under catalytic conditions is known (complexes with different ligands, Coucouvanis and Lane, 1991) to form a dimer under the conditions employed where precipitation is forced under high concentration. Due to the nature of cyanide, it is therefore inseparable to isolate the asymmetric complexes as exclusively catalytic treatment.

Thus, a nontoxic compound will show no effects compared to the unreacted control. A toxic compound will show less ATP activity than cyanide, as is shown for CoCl$_2$. The compound according to the invention appears non-toxic, and when combined with thiosulfate excellent survival is achieved. The same compound was administered in an escalation dose study in mice. We found 50 mg/Kg as a safe dose of this compound in mice. In comparison, ibuprofen safe dose for children is 10 mg/Kg (drugs.com).

The toxicity and pharmaceutical acceptability is dependent on the ligand of the molybdenum compound. Accordingly, the present inventors have provided molybdenum compounds with ligands, which provide a low toxicity, rendering them especially suitable for use in the treatment of cyanide poisoning in mammals and in particular humans.

Traditional cyanide treatments and current novel treatments that are either new or in clinical trials were discussed in background of the invention above. The common cyanide treatments have, as mentioned above in common, that they are not suitable for acute poisoning, or for treatment of a large group of victims simply because they are either labor intensive and require training to administer, or carry risk to the victim by themselves, or even prohibitively expensive.

Clinically, the availability of sufficient cyanide treatments in ambulances and emergency responder kits, in the form of e.g. epi pens or a similar device, to treat a group of people on site will add a new capability to treat smoke inhalation victims and casualties in industrial accidents quickly and safely. An epi pen is a device, which contain a spring-loaded needle that exits the tip of the device (in some cases through a sterile membrane) and penetrates the recipient's skin, to deliver the medication via subcutaneous or intramuscular injection. Currently, most Emergency Rooms have at most a single kit to treat one person for cyanide poisoning using intravenous administration.

The present inventors have developed molybdenum compounds, compositions and kit comprising such molybdenum compounds for use in the treatment of cyanide poisoning, which catalytically forms thiocyanate in the presence of cyanide and, thus, requires only a small amount of compound (minimal toxicity). A number of victims may be treated quickly without special training with an IM administration. The treatment is a small molecule, molybdenum sulfur compound that would be administered with thiosulfate and acts without sacrifying oxygen transport. Preliminary data shows that 83% of the cyanide was removed from a solution, as thiocyanate, in 20 minutes. It is estimated that death from cyanide poisoning occurs within one hour at toxic inhalation levels. 83% reduction in cyanide levels is a change from lethal toxicity to a low-level toxicity.

Novel Molybdenum Compounds and their Use for Treating Cyanide Poisoning

Thus, in a first aspect the present invention provides a novel molybdenum compound having the following formula:

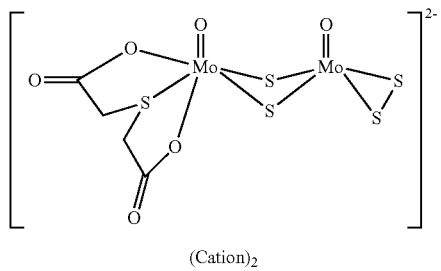

(Cation)$_2$

The novel molybdenum compound according to the present invention can be in the form of any suitable salt. The salt may preferably be any pharmaceutically acceptable salt.

In one embodiment, the novel compound of the present invention is provided as a salt, wherein the cation is selected from the group consisting of sodium, potassium, R$_4$N, wherein R is selected from hydrogen, methyl, ethyl, propyl, or Butyl, meglumine, glucosamine, ethanolamine, diethanolamine, triethanolamine (TEA), tromethamine (TRIS), N-methylaminoethanol, and N,N-dimethylaminoethanol.

In another embodiment, the novel molybdenum compound according to the present invention provides for the use of the novel compound and any pharmaceutically acceptable salt thereof in the treatment of cyanide poisoning in a mammal. In one embodiment, the mammal is a domestic animal. In another embodiment the mammal is a farm animal. In a particular embodiment, the mammal is a human being.

Compositions Comprising Molybdenum for Use in the Treatment of Cyanide Poisoning The present invention also relates to compositions comprising molybdenum compounds for use in the treatment of cyanide poisoning.

Thus in one aspect, the present invention provides a composition comprising a molybdenum compound according to the following formula,

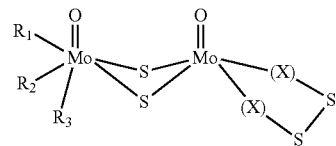

Wherein
X is S or a bond; and
R$_1$, R$_2$, and R$_3$ independently or together are one or more of the ligands selected from the group consisting of: a mono- or disaccharide having 3 to 12 carbon atoms, a natural amino acid, a primary, secondary, or tertiary amine, substituted with an alkyl having 1 to 5 carbon atoms, a mono- or di-carboxylic acid having 1 to 5 carbon atoms, which may be substituted with O, S, CH$_3$S— or N, a thiocarboxylic acid having 1 to 5 carbon atoms, a primary, secondary or tertiary amide having 1 to 5 carbon atoms, wherein the side chains attached to the nitrogen is an alkyl having 1 to 5 carbon atoms, a complexing agent, such as EDTA, cyanide, thiocyanate (SCN$^-$), sulfite, disulfide or tetrasulfide, and wherein R$_3$ may be an electron pair; for use in the treatment of cyanide poisoning in a mammal.

In a particular embodiment, the present invention provides a composition comprising a molybdenum compound having the formula:

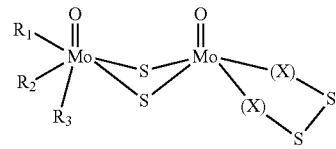

wherein X is S or a bond; and
wherein R$_1$, R$_2$, and R$_3$ independently or taken together are one or more of the ligands selected from the group consisting of: methionine, cysteine, threonine, serine, glutamate, malate, oxalate, methylsulfenyl succinate, mercapto succinate, dimethylformamide (DMF), cyanide, thiocyanate, thiosulfate, sulfite, disulfide or tetrasulfide, acetate, thiodiacetic acid, ammonium or diethylamine, and wherein R$_3$ may be an electron pair;
for use in the treatment of cyanide poisoning in a mammal.

In an embodiment of the present invention, the composition comprises a molybdenum compound, wherein X is a bond. In another embodiment, X is S.

In yet another aspect, the present invention provides a composition comprising a molybdenum compound, wherein the molybdenum compound has the formula:

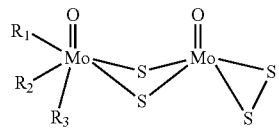

wherein R$_1$, R$_2$, and R$_3$ independently or taken together are one or more of the ligands selected from the group consisting of: methionine, cysteine, threonine, serine, glutamate, malate, oxalate, methylsulfenyl succinate, mercapto succinate, dimethylformamide (DMF), cyanide, thiocyanate, thiosulfate, sulfite, disulfide or tetrasulfide, acetate, thiodiacetic acid, ammonium or diethylamine and wherein $R_3$ may be an electron pair;

for use in the treatment of cyanide poisoning in a mammal.

In a further embodiment, the present invention provides a composition comprising a molybdenum compound having the formula:

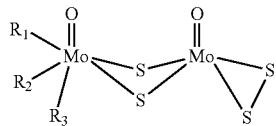

wherein $R_1$, $R_2$, and $R_3$ taken together are one of the ligands selected from the group consisting of: methionine, cysteine, threonine, serine, glutamate, malate, oxalate, methylsulfenyl succinate, mercapto succinate, dimethylformamide (DMF), cyanide, thiocyanate, thiosulfate, sulfite, disulfide or tetrasulfide, acetate, thiodiacetic acid, ammonium or diethylamine, and wherein $R_3$ for use in the treatment of cyanide poisoning in a mammal.

The compositions according to may be in the form of a pharmaceutically acceptable salt suitable for intravenous or intramuscular administration.

Hence, in one aspect, the compositions of the present invention are in the form of a salt having a cation selected from the group consisting of sodium, potassium and $R_4N$, wherein R is either hydrogen, methyl, ethyl, propyl, or Butyl, meglumine, glucosamine, ethanolamine, diethanolamine, triethanolamine (TEA), tromethamine (TRIS), N-methylaminoethanol, or N,N-dimethylaminoethanol.

In relation to the present invention the terms "amino acid" or natural amino acid mean any common or naturally occurring amino acid or dertivatives thereof including glycine, alanine, valine, leucine, isoleucine, serine, cysteine, selenocysteine, threonine, methionine, proline, phenylalanine, tyrosine, tryptophan, histidine, lysine, arginine, aspartate, glutamate, asparagine, glutamine, and ornithine.

The composition comprising a molybdenum compound according to the present invention may either be used for the stoichiometric treatment of cyanide poisoning, wherein the molybdenum compound reacts stoichiometrically with cyanide present in the body to form thiocyanate, or for catalytic treatment of cyanide poisoning, wherein the molybdenum compound catalyses the conversion of cyanide to thiocyanate ($SCN^-$) using a sulfur donor.

Thus, in one aspect, the compositions according to the present invention are provided, wherein the molybdenum compound is administered at a dose between 0.5 and 50 mg per kg body weight, such as between 1 and 50 mg, 2 and 50 mg, such as between 3 and 50 mg, 4 and 50 mg, 5 and 50 mg, 7.5 and 50 mg, 10 and 50 mg, 15 and 50 mg, 20 and 50 mg, 25 and 50 mg or between 1 and 45 mg, 2 and 40 mg, 3 and 35 mg, 4 and 30 mg, 5 and 25 mg, 10 and 20 mg, 15 and 20 mg per kilo body weight.

As mentioned above, the composition according to the present invention may in addition comprise a sulfur source in which case the molybdenum compound functions as a catalyst facilitating the transfer of sulfur from the sulfur source to cyanide in order to form thiocyanate ($SCN^-$).

Hence, in a further aspect, the present invention provides a composition, which in addition to the abovementioned molybdenum compound comprises a sulfur source. In a further embodiment the sulfur source is selected from the group consisting of: sulfur, thiosulfate, ammonium sulphide, dithiothreitol (DTT), trithiothreitol, gluthathione, or dibenzyl trisulfide (DTS).

In a particular embodiment, the sulfur source is a salt selected from the group consisting of sodium thiosulfate or potassium thiosulfate.

Thus, in a further aspect, the present invention provides a composition, wherein the molybdenum compound is administered at a dose between 0.25 and 25 mg per kilo body weight in combination with a sulfur source at a dose between 10 and 250 mg per kilo body weight. In one embodiment, the molybdenum compound is administered at dose between 1 and 20 mg, such as 2 and 15 mg, such as 3 and 10 mg, such as 4 and 10 mg, such as 5 and 10 mg per kilo body weight and the sulfur source is administered at a dose between 20 and 225 mg, such as 30 and 175 mg, such as 40 and 150 mg, such as 50 and 125 mg, such as 75 and 100 mg per kilo body weight.

The compositions of the present invention may be formulated in solid form for dissolution prior to administration. In the alternative, the compositions of the present invention are formulated as a liquid solution or suspension.

Moreover, the compositions of the present invention may be administered by intravenous administration, nasal administration, intra-peritoneal administration or intramuscular administration.

The compositions of the present invention are suitable for treating cyanide poisoning in mammals, including domestic animal, farm animals and in particular humans.

In addition, the compositions according to the present invention may further comprise pharmaceutically acceptable excipients, vehicles or other pharmaceutically acceptable adjuvants.

Also, the compositions of the invention may comprise one or more further pharmaceutically active substances.

Kits for Use in the Treatment of Cyanide Poisoning

As mentioned above, clinically, the availability of sufficient cyanide treatments in ambulances and emergency responder kits, e.g. in the form of epi pens or a similar device, to treat a group of people on site will add a new capability to treat smoke inhalation victims and casualties in industrial accidents quickly and safely.

Thus, in another aspect, the present invention provides a kit comprising compound or a composition according to the present invention for use in the treatment of cyanide poisoning.

In a further embodiment, the kit is in the form of an epi pen or similar design, i.e. an epi pen or similar device, which contain a spring-loaded needle that exits the tip of the device (in some cases through a sterile membrane) and penetrates the recipient's skin, to deliver the medication via subcutaneous or intramuscular injection.

Methods of Treating Cyanide Poisoning

Furthermore, the present invention provides methods of treating cyanide poisoning in a mammal, such as a domestic animal, a farm animal or, in particular, a human, said methods comprising administering a therapeutically effective amount of a molybdenum compound of the present invention, a composition comprising a molybdenum compound as mentioned above or a kit as mentioned above.

The method of treating cyanide poisoning comprising administration of a molybdenum compound according to the present invention may either be a stoichiometric treatment of the cyanide poisoning, wherein the molybdenum compound reacts stoichiometrically with cyanide present in the body to form thiocyanate, or a catalytic treatment of cyanide poisoning, wherein the molybdenum compound catalyses the conversion of cyanide to thiocyanate (SCN⁻) using a sulfur donor.

Processes for the Preparation of Molybdenum Compounds

The present invention also provides a process for the preparation of the novel molybdenum compounds of the invention.

Thus, in yet another aspect, the present invention provides a process for preparing the molybdenum compound having the formula,

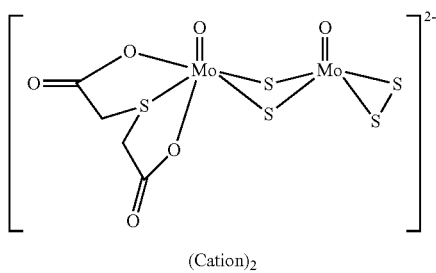

(Cation)₂ comprising:

1) suspension of a molybdenum compound having the following formula

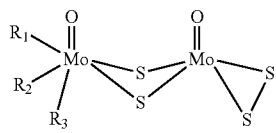

wherein $R_1$, $R_2$, and $R_3$ independently or together are one or more of the ligands selected from the group consisting of: a mono- or disaccharide having 3 to 12 carbon atoms, a natural amino acid, a primary, secondary, or tertiary amine, substituted with an alkyl having 1 to 5 carbon atoms, a mono- or di-carboxylic acid having 1 to 5 carbon atoms, which may be substituted with O, S, CH₃S— or N, a thiocarboxylic acid having 1 to 5 carbon atoms, a primary, secondary or tertiary amide having 1 to 5 carbon atoms, wherein the side chains attached to the nitrogen is an alkyl having 1 to 5 carbon atoms, a complexing agent, such as EDTA, cyanide, thiocyanate (SCN⁻), sulfite or tetrasulfide, and wherein $R_3$ may be an electron pair, in an inert solvent under an inert atmosphere;

2) addition of 2,2'-thiodiacetic acid in the presence of a base in a dry inert solvent under inert atmosphere and stirring the reaction mixture;

3) evaporation of the solvent and precipitation;

4) wash of precipitate with ethanol and ether, and optionally re-crystallisation; and 5) providing the molybdenum compound having the following formula:

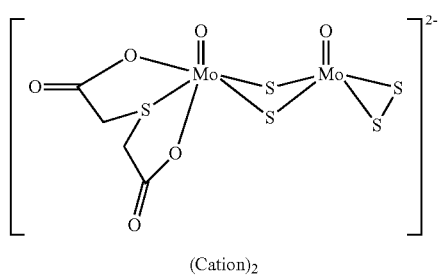

(Cation)₂

The above process may be performed, wherein, in step 1), $R_1$, $R_2$, and $R_3$ independently or taken together are one or more of the ligands selected from the group consisting of: methionine, cysteine, threonine, serine, glutamate, malate, oxalate, methylsulfenyl succinate, mercapto succinate, dimethylformamide (DMF), cyanide, thiocyanate, thiosulfate, sulfite or tetrasulfide, ammonium or diethylamine, and wherein $R_3$ may be an electron pair.

The process according to the present invention may be performed using a base in step 2) selected from the group consisting of NaOH, KOH, CsOH, ᵗBuOK, ᵗBuONa, NaOMe, KOMe, ᶦPrONa Na₂CO₃, K₂CO₃, Et₄NOH, and Bu₄NOH.

Moreover, the inert solvent mentioned in step 1) and 2) may be selected from the group consisting of acetonitrile, water, DMF, acetone, THF, ethanol, methanol, DMSO (dimethyl sulfoxide), dioxane, DME (dimethoxyketone), glycol, and MEK (methylethylketone) and any combination thereof. The inert atmosphere of step 1) and 2) may furthermore be either argon or nitrogen.

The reaction mixture under step 2) of the process may be stirred for 10 minutes to 2 hours, preferably 30-60 minutes, such as 30 minutes or 45 minutes at a temperature between 0° C. and the boiling point of the solvent used, such as between 0° C. and 50° C., such as between 10° C. and 30° C., preferably between 20° C. and 25° C.

In a particular embodiment, the process of the present invention is provided wherein, in the starting compound of step 1), $R_1$, $R_2$ and $R_3$ together are DMF.

The above process is generally applicable in the preparation of the molybdenum compounds of the present invention as is also evident from the synthesis examples by using the ligand molecule to be attached in the final product as R1, R2, and R3 instead of 2,2'-thiodiacetic acid in step 2) of the said process using e.g. the above starting compound in step 1), wherein R1, R2 and R3 together are DMF, or any other suitable starting compound as mentioned above.

Thus, in a further embodiment, the above process of the present invention can be used for the preparation of a molybdenum compound having the formula:

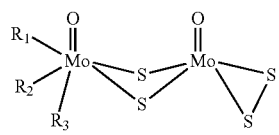

Wherein $R_1$, $R_2$, and $R_3$ taken together are selected from the group consisting of cysteine, methionine, serine, or threonine by using cysteine, methionine, serine, or threonine instead of 2,2'-thiodiacetic acid in step 2) of the above process, and wherein the starting compound in 1) may be [Mo₂O₂S₄(DMF)₃].

According to another aspect of the invention, other organosoluble salts of the complexes can be formed upon performing metathesis reactions. For example, a salt based on $Ph_4P+$ can be formed in this way.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

EXAMPLES

The synthesis examples 1 and 2 were performed under nitrogen or argon unless otherwise stated. The complex $(Et_4N)_2[Mo_2O_2S_8]$ was synthesized as described in literature. (Coucouvanis and Toupadakis 1988). From $(Et_4N)_2[Mo_2O_2S_8]$, the complex $[Mo_2O_2S_4(DMF)_3]$ was synthesized according to literature (Coucouvanis and Lane 1991) and used as the starting material for the synthesis of a series of novel complexes following a general method as described below.

Bases used in the synthesis examples are hydroxides (sodium, potassium, cesium), $^tBuOK$, or $^tBuONa$, or methoxides (NaOMe, KOMe, $^iPrONa$), carbonates ($Na_2CO_3$, $K_2CO_3$), organic hydroxides ($Et_4NOH$, $Bu_4NOH$) etc. Countercations are $Na^+$, $K^+$, $Et_4N^+$, $Bu_4N^+$, accordingly.

Solvents are acetonitrile, water or DMF depending on the ligand, and the countercation.

Example 1

Method A; Synthesis of $[Mo_2O_2S_4(C_4H_4O_4S)]^{2-}$ Potassium Salt.

The $[Mo_2O_2S_4(DMF)_3]$ (0.5 g, 0.87 mmol) was suspended in 40 ml distilled and degassed DMF under argon. To this solution was added a mixture of 2,2'-thiodiacetic acid (0.13 g, 0.87 mmol) and $^tBuOK$ (0.2 g, 1.75 mmol) in dry methanol under argon. The resulting solution was stirred 30 minutes, the solvent removed in vacuo, and the dark red solid washed with ethanol and ether. The residue was redissolved in 50 ml dry DMF, filtered and precipitated with isopropanol. The dark red solid was isolated by filtration and dried in vacuum. Yield 0.27 g (60%).

Method B, Synthesis of $[Mo_2O_2S_4(C_4H_4O_4S)]^{2-}$ Sodium Salt.

The $(Et_4N)_2[Mo_2O_2S_8]$ (0.5 g, 0.67 mmol) was suspended in 40 ml DMF. To this solution was added iodine (0.17 g, 0.67 mmol) dissolved in 25 ml DMF. After the iodine addition was complete, a mixture of sodium carbonate (0.14 g, 1.34 mmol) and 2,2'-thiodiacetic acid (0.10 g, 0.67 mmol) in 12 ml methanol was added. The resulting solution was stirred 2 hours, filtered, and the solvent removed in vacuum. The solid obtained was washed with alcohol, redissolved in 30 ml dry DMF, filtered and precipitated with ether. The dark red solid was isolated by filtration and dried in vacuo. Yield 0.19 g (50%).

FT-IR(KBr): $n(CO_2^-)$ 1658 (vs), $\nu(Mo=O)$; 927(s), $n(S_2^{2-})$521(m), $n(Mo-S_b)$462(w). $^1H$-NMR(dmso-$d_6$): 3.5 (broad). UV/visible; e, $M^{-1}cm^{-1}$: 312(13170), 464(1800).

Compounds of the formula $(cat)_m[Mo_2O_2S_4(L)_n]$ were synthesized using similar methods where L is a mono, bi, or tridentate ligand, and n is accordingly 1, 2 or 3. Number of cations m depends on the total charge induced by L or n*L. The following compounds may for instance be prepared by using method A, Wherein 2,2'-thiodiacetic acid has been substituted with L in a suitable amount:

L=methionine. FT-IR(KBr): $\nu(CO_2^-)$1649 (vs), $\nu(Mo=O)$; 924(s), $\nu(S_2^{2-})$519(m), $\nu(Mo-S_b)$465(w).

L=serine. FT-IR(KBr): $\nu(CO_2^-)$1629 (vs), $\nu(Mo=O)$; 937(s), $\nu(S_2^{2-})$510(m), $\nu(Mo-S_b)$463(w).

L=threonine. FT-IR(KBr): $\nu(CO_2^-)$1649 (vs), $\nu(Mo=O)$; 933(s), $\nu(S_2^{2-})$514(m), $\nu(Mo-S_b)$465(w).

Air-Stable Synthetic Route:

Air-stable synthetic route was established using water as a solvent.

General procedure: $[Mo_2O_2S_4(DMF)_3]$ (0.5 g, 0.87 mmol) is suspended in water (20 ml). Leucine (0.12 g, 0.87 mmol) and $Na_2CO_3.10H_2O$ (0.12 g, 0.435 mmol) are mixed together in 10 ml water. When all is dissolved and bubbling has stopped, the solution is added dropwise to the suspension of $[Mo_2O_2S_4(DMF)_3]$. The suspension dissolves to form a clear red solution, that is taken to dryness and the red solid collected onto a fritted funnel and washed with acetone and ether. Air dried and the compound is lyophilized to give 0.41 g of red solid (90%)

L=leucine; FT-IR (KBr): $\nu(CO_2^-)$ 1621 (vs), 1386(ms), $\nu(M=O)$ 948(s), 930(s), $\nu(S_2^{2-})$ 521(w), $\nu(S^{2-})_b$ 481(w)

L=cysteine; FT-IR(KBr): $\nu(CO_2^-)$ 1636 (vs), 1371(ms), $\nu(M=O)$ 945(s), 929(s), $\nu(S_2^{2-})$ 526 (w), $\nu(S^{2-})_b$ 466(w)

L=oxalate; FT-IR (KBr): $\nu(CO_2^-)$ 1594 (vs), 1371 (ms), $\nu(M=O)$ 944(s), 926(s), $\nu(S_2^{2-})$521 (w), $\nu(S^{2-})_b$ 464(w)

Example 2

Synthesis of $[Mo_2O_2S_2(NCS)_4]^{2-}$. Tetraethylammonium Salt.

The $(Et_4N)_2[Mo_2O_2S_8]$ (0.5 g, 0.67 mmol) and KSCN (0.25 g, 2.56 mmol) were suspended in 60 ml DMF in the air. To this solution was added iodine (0.34 g, 1.24 mmol) dissolved in 30 ml DMF. After the iodine addition was complete, the resulting solution was stirred 2 hours, filtered, and the product precipitated by addition of ethanol. The solid obtained was isolated by filtration and dried in vacuo. Recrystallization from acetonitrile/ethanol afforded the product as a red microcrystalline solid. Yield 0.45 g (80%).

FT-IR (KBr, $cm^{-1}$: $\nu(NCS^-)$ 2083, (vs), $\nu(Mo=O)$ 949; $\nu(Mo-S_b)$ 472. UV/visible; e, $M^{-1}cm^{-1}$: 308(12300), 350 (sh). MS-ESI: m/z; $[M^{2-}+Et_4N^+]^-$: 709.55, $[M^+-(Et_4N++SCN^-)]^-$; 650.82

Example 3

In Vitro Study of the Molybdenum Compounds of the Present Invention as Catalysts in Reactions of Cyanide with Thiosulfate.

Catalytic Activity Testing:

Solutions of the compound to be studied were prepared at concentrations of 1 mM in veronal buffer. Veronal buffer (pH 7.4) was prepared as stock solution. Thiosulfate solutions were prepared in 18 MΩ·cm Milli-Q water prior to use. The reactions were performed by first adding thiosulfate to the compound solution, followed by addition of cyanide. The reactions were performed at 25° C. in sealed tubes. Reaction times were recorded starting from the time of addition of cyanide. Samples were withdrawn at regular time intervals. A sample of all components except for cyanide was used as a blank. Thiocyanate formed was quantitated colorimetrically using $FeSCN^{2+}$ calibration curve and measuring its absorbance at 447 nm. Total concentration of cyanide was determined at the start and at the end of the reaction, to confirm that the cyanide had not volatilized during the experiment. Sampling and preparation of samples for analysis was carried out in a well-ventilated hood.

Reactions at pH of 9.2 were run similarly using a carbonate buffer. Studies on the influence of thiosulfate to cyanide ratio present in solution on the rate of thiocyanate formation were performed similarly with the appropriate reagent concentrations. Catalyst concentrations were kept at 10% (mol) for all the studies for practical reasons, and the cyanide and thiosulfate concentrations changed. Study of cyanide and thiosulfate reactivity alone was performed similarly minus the catalyst. Ionic strength of the solutions was calculated to about 0.2 M. Stoichiometric Activity Testing: Solutions of the compound to be studied were prepared at concentrations of 1 mM in veronal buffer. Veronal buffer (pH 7.4) was prepared as stock solution. The cyanide solution was added to the compound solution. The reactions were performed at 25° C. in sealed tubes. Reaction times were recorded starting from the time of addition of cyanide. A sample of all components except for cyanide was used as a blank. Samples were withdrawn at regular time intervals. Thiocyanate formed was quantitated colorimetrically using $FeSCN^{2+}$ calibration curve. Total concentration of cyanide was determined at the start and at the end of the reaction, to confirm the cyanide had not volatilized during the experiment. Sampling and preparation of samples for analysis was carried out in a well-ventilated hood. Reactions at pH of 9.2 were run similarly using a carbonate buffer.

Quantitation of Cyanide. A colorimetric method described in ASTM 2036 (method D) was used to quantitate cyanide concentrations in aqueous solutions. This method was used in reactivity studies of various compounds with cyanide. The molybdenum compounds tested do not absorb above 450 nm. The samples prepared using this compound absorb at 582 nm and therefore do not interfere with other colored species present. Color stability is for a few hours, and the solutions were analyzed within 30 minutes of color development. Calibration curves were prepared by accurately weighing 0.651 g of potassium cyanide and dissolving in 10 ml 0.1 M NaOH. Dilutions were carried out to obtain standards in the concentration range of 0.2 mM to 1.0 mM.

Figures 1A, 1B:
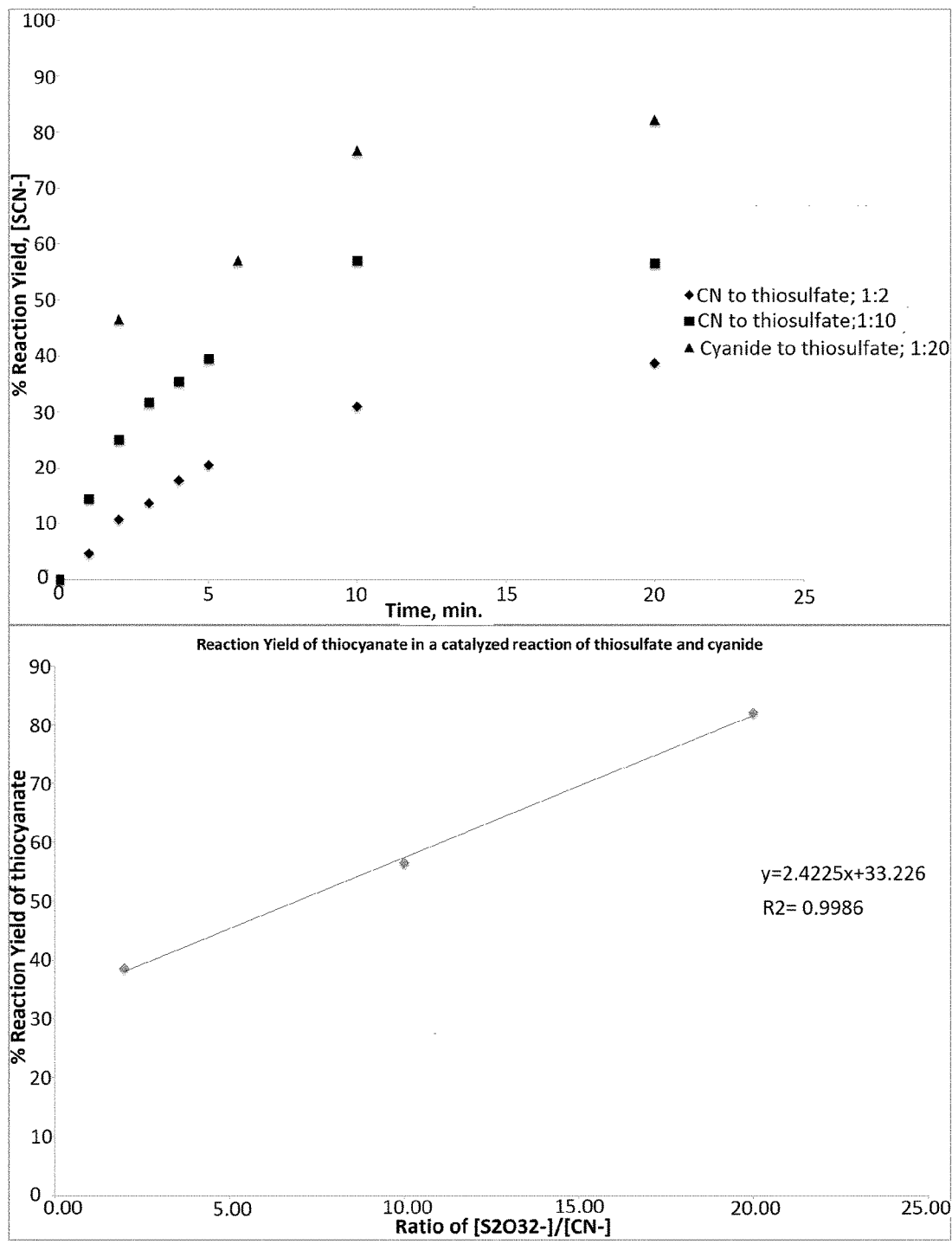
FIG. 1A shows the conversion of cyanide to thiocyanate, which is shown as a function of time for three different ratios of thiosulfate to cyanide.
FIG. 1B shows the 20 min data from chart 1 plotted as reaction yield as a function of ratio.

The results are shown in FIGS. 1A, 1B, and 2.

Results from stoichiometric reactions of model complexes with cyanide buffered at two different pH values are shown in table 1 below.

Stoichiometric Activity Testing:

The complexes according to the invention listed in table 2 below reacted with one equivalent of cyanide to form one equivalent of thiocyanate after one hour reaction time in veronal buffer at pH 7.4. The thiocyanate formed was determined as $FeSCN^{2+}$ against a calibration curve. For comparison, a complex (entry 2 in table 2) was also measured, but this complex was not expected to form thiocyanate since it does not have any available sulfurs.

TABLE 2

Shows thiocyanate formation for several complexes in buffered solution at pH 7.4.

| Nr | Complex | Calc. Concentration $[complex]_{(aq)}$ (mM) | Measured Concentration $[SCN^-]_{(aq)}$ (mM) |
|---|---|---|---|
| 1 | $Mo_2O_2S_4(DMF)_3$ | 0.093 | 0.140 |
| 2 | $K_2[Mo_2O_2S_2(cys)_2]$ | 0.101 | 0.000 |
| 3 | $(Et_4N)[CpMo_2O_2S_4]$ | 0.093 | 0.095 |
| 4 | $(Et_4N)[Mo_2O_2S_4(leu)]$ | 0.083 | 0.082 |
| 5 | $Na[Mo_2O_2S_4(met)]$ | 0.102 | 0.108 |

Example 4

Toxicity and Efficacy Studies of Molybdenum Compounds of the Invention Hepatocyte Model.

Hepatocytes were chosen because of their robustness towards cyanide. Hepatocytes contain rhodanese, therefore appropriate controls were used to evaluate the background from the natural activity of rhodanese in the cells. The efficacy studies employed control protocols to evaluate performance of the sulfur donor and were designed to evaluate ATP levels in primary hepatocytes for:
Thiosulfate and cyanide
Molybdenum sulfur compound
Molybdenum sulfur compound and cyanide
Molybdenum sulfur compound, thiosulfate and cyanide A nontoxic compound with the rhodanese will either show no effect compared to the rhodanese and thiosulfate controls, or improve the sulfur transfer compared to the thiosulfate control after exposure to cyanide, resulting in restored ATP activity. In this model, efficacy is observed qualitatively

TABLE 1

| pH 9.2 Amount of cyanide reacted in equivalents per mole complex (x) | Amounts of thiocyanate formed in equivalents per mole complex | | |
|---|---|---|---|
| | $(Et_4N)_2[MoOS_8]^{2-}$ (1) | $(Et_4N)_2[Mo_2O_2S_8]^{2-}$, (2) | $[Mo_2O_2S_4(DMF)_3]$, (3) |
| 1 | 0.9 | 0.85 | 0.91 |
| 6 | >2 | >2 | 0.91 |

| pH 7.4 Amount of cyanide reacted in equivalents per mole complex (x) | Amounts of thiocyanate formed in equivalents per mole complex | | |
|---|---|---|---|
| | $(Et_4N)_2[MoOS_8]$ (1) | $(Et_4N)_2[Mo_2O_2S_8]^{2-}$, (2) | $[Mo_2O_2S_4(DMF)_3]$, (3) |
| 1 | 0.5 | 0.28 | 0.56 |
| 6 | >2 | >2 | 0.56 |

Note:
Compounds (1) and (2) formed very turbid solutions under the conditions used with larger amounts of cyanide.

based on improved cell survival compared to the cyanide only experiment (background). Concentrations were chosen to target 50% cell death under our conditions to allow for observation of either improved or reduced cell death.

Experimental Procedure.

For the in vitro evaluation of cyanide antidotes, rat hepatocytes were isolated by well-established procedures and cultured as monolayers using published method. (S. J. Gee, C. E. Green, and C. A. Tyson. *Cyanide-induced cytotoxicity to isolated hepatocytes. Toxic. In Vitro*, 4, 37-45 (1990)). Studies with this model have demonstrated reproducible efficacy of known cyanide antidotes, using ATP depression as the endpoint.

Hepatocytes were isolated from a Sprague-Dawley rat and plated (10,000 cells/well) on to a BD Biosciences 96-well BioCoat Collagen I plate. Cells were allowed to attach for approximately 2 hours, then culture media exchanged to remove dead and unattached cells. Cells were incubated in 200 ml culture media at 37° C. under air:$CO_2$ (95:5) overnight to recover and stabilize ATP activity. The reaction involved preincubating cells with 1 mM KCN in 100 ml of culture media for 10 min, followed by addition of test compounds at 3 different concentrations (50 ml) and sodium thiosulfate (50 ml) at a final concentration of 5 mM in a 200 ml incubation volume.

After the addition of test articles and thiosulfate at 0.5, 1 and 2 hrs (a separate incubation plate to be used for each time point), media was removed from each well and replaced with 200 ml ice-cold 1% Trichloroacetic acid (TCA) containing xylenol blue dye to lyse and extract ATP. ATP present in the lysate was measured using the luciferin/luciferase reaction in the ENLITEN ATP assay. Published studies suggested that 60 min after antidote addition excellent sensitivity and dose dependence of antidote effect is obtained. (See C. E. Green, S. E. LeValley, and C. A. Tyson. *Comparison of amphetamine metabolism using isolated hepatocytes from five species including humans. J. Pharmacol. Exp. Therap.* 237, 931-936 (1986)).

The experiment was repeated at least 3 times to obtain standard errors on the data points.

The results of the safety study are shown in FIGS. 3, 4, 5, and 6.

The results of the combined safety and efficacy study are summarized in table 3 below and illustrated graphically in FIG. 7.

TABLE 3

| Test compound* | % Survival |
| --- | --- |
| CN + $CoCl_2$ + thiosulfate | 43.73 |
| CN + $CoCl_2$ | 41.16 |
| CN + antidote | 56.6 |
| CN + antidote + thiosulfate | 84.35 |
| Thiosulfate only | 63.17 |
| Cyanide (CN) only | 55.8 |
| Antidote only | 95.3 |
| Blank control | 100 |

*Incubation Conditions - 10,000 cells/well, 1 mM Potassium Cyanide, 5 mM sodium thiosulfate, 0.15 mM $K_2[Mo_2O_2S_4(C_4H_4O_4S)]$ (antidote) or 0.15 mM $CoCl_2$ for 1 hr at 37° C. Cells were freshly isolated hepatocytes from Sprague Dawley rats.

It can be seen that Cyanide exposed cells lose ATP activity to ~55%. Thiosulfate showed antidotal effect on the recovery of ATP activity in cyanide exposed cells to 63%. There was no significant increase in ATP activity in the presence of $K_2[Mo_2O_2S_4(C_4H_4O_4S)]$ alone (~56%) compared to cyanide exposed cells (~55%), whereas there is an enhanced recovery of ATP activity in cyanide exposed cells in the presence of thiosulfate and $K_2[Mo_2O_2S_4(C_4H_4O_4S)]$ (antidote) of around 84%. However, no significant antidotal effect of $CoCl_2$ at 0.15 mM either with or without the presence of thiosulfate on cyanide exposed cells at 1 hr. (reference compound). Moreover, there is no significant effect of antidote at 0.15 mM on ATP levels in the cells (~95%) that have not been exposed to cyanide.

Example 5

In Vitro Studies of Compounds.

In vitro studies of compounds according to the invention were conducted in three difference cancer cell lines to evaluate the toxicity of the compounds. The cancer cell lines were chosen since they are already sensitive and likely to show maximum potential toxicity. The cell lines selected were MCF-45 (breast cancer), PT45 (pancreatic cancer), and HT29 (colon cancer). Known compounds were used as reference compounds. Table 4 below shows the data obtained.

The compounds employed in the in vitro toxicity studies are shown below. Cis-platin was used as a reference compound.

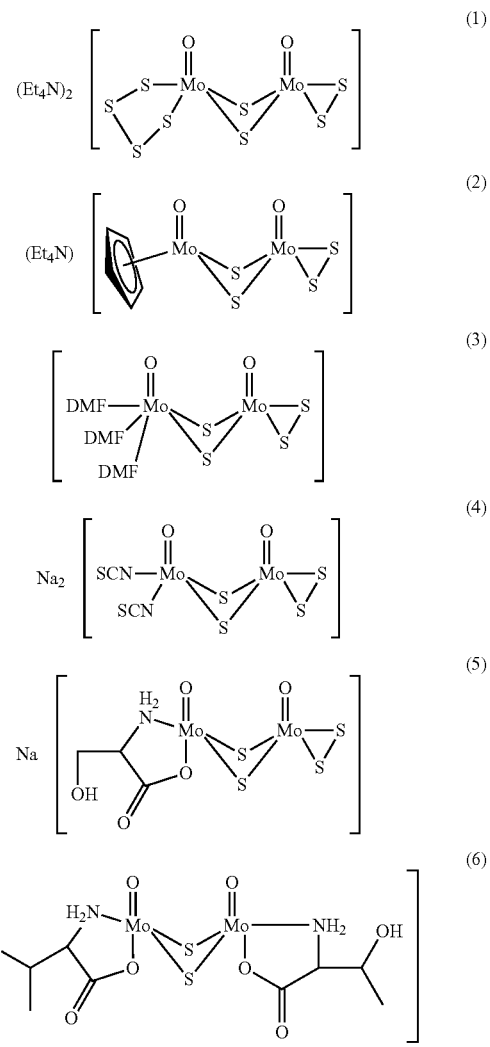

-continued

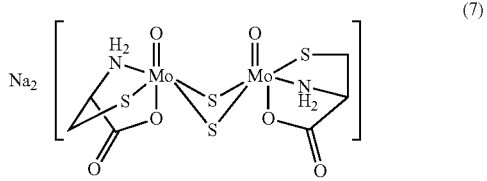

(7)

The most toxic compound (entry 1) is 80 times less toxic than cisplatin, and the least toxic compound studied (entry 7) is 800 times less toxic. The results show the compounds appear non-toxic to cells.

TABLE 4

The table shows IC$_{50}$ values (μM) obtained for complexes 1-7 in three different cell lines after treating the cells for 72 hours and assayed with the MTT (tetrazolium dye) method. Values for each measurement in the table are averages for four repeats. Entry no. 8 is cisplatin reference compound.

|  | Cell Line | | |
|---|---|---|---|
| Complex no. | MCF-7 | PT45 | HT29 |
| 1 | 86 ± 11 | 36 ± 7 | 53 ± 2 |
| 2 | 262 ± 110 | 83 ± 5 | 374 ± 191 |
| 3 | 376 ± 176 | 114 ± 25 | 126 ± 15 |
| 4 | 198 ± 43 | 35 ± 2 | 327 ± 57 |
| 5 | 271 ± 71 | 66 ± 7 | 167 ± 29 |
| 6 | 739 ± 347 | 108 ± 14 | 590 ± 91 |
| 7 | 822 ± 302 | 179 ± 32 | — |
| 8 | 1.6 ± 0.36 | 0.80 ± 0.15 | 1.0 ± 0.20 |

Protocol: Cancer cell lines used: PT45 (pancreas cancer), MCF-7 (breast cancer) and HT29 (colon cancer).

Cell splitting: Each cell type was incubated in medium at 37° C., and 10% $CO_2$. Dulbecco's Modified Eagle Medium (DMEM) was employed ([+] 4.5 g/L D-Glucose, [+] L-Glutamine, [−] Pyruvate in 10% Fetal Calf Serum). The medium was removed and the cells were washed with Dulbecco's Phosphate Buffered Saline solution. Two mL of trypsin EDTA solution were added to each petri dish and incubated until the cells were loose from the surface. Eight mL of DMEM were added to each plate and mixed well and transferred to centrifuge tubes. The cell suspensions were centrifuged, the medium removed and 10 mL of fresh medium added to each tube. The pallettes obtained were vortexed in the new medium. Cell counting of the resulting cell suspensions was done with a Bio-rad TC10™ Automated Cell Counter. With this method, $7.6 \cdot 10^5$ cells/mL to $8.6 \cdot 10^5$ cells/mL were obtained. Part of the cell suspensions were further diluted and incubated for growth and future use.

Cell Plating: Stock solutions for each cell line were prepared. Dilutions were performed to get a concentration of approximately 6000 cells/100 μL of medium. In these experiments 96-well plates were used. One hundred microliters was added of each cell line stock solution to four consecutive columns (eight consecutive rows) and diluted 8 times by row. As many plates as are needed were prepared this way and incubated for 24 h.

Treating of Cells with Compounds: Seven compounds were tested for toxicity on the three different cell lines. Each of the compound was dissolved in either water or DMSO to form 10 mM solutions. Those stock solutions were further diluted to form stock solutions with eight different concentrations for each compound. For each compound, three plates were treated. After treating the cells with the compounds, the plates were incubated for 24 h, 48 h and 72 h. Precision was taken in writing down exactly when each plate was treated.

MTT Assay: Cell viability was measured for each compound using an MTT assay at 24 h, 48 h and 72 h timepoints. After MTT solution (2.5 mg/mL) were added to each well, they were further incubated for two hours. The media was removed and 200 μL of DMSO were added to each well. The absorption of each well was measured at 550 nm (vs background at 620 nm) and used to calculate IC$_{50}$ values of each compound. The IC$_{50}$ values were determined using GraphPad Prism software.

Example 6

Solubility Determination of Compounds.

Solubility was determined for five different compounds to evaluate their aqueous solubility. The solubility was determined by preparing a saturated solution of the compound, and diluting the supernatant sample to obtain absorbance of 1 a.u. or less, and calculating the concentration based on the pre-determined molar extinction coefficient. The concentrations were then converted to units of g/L by multiplying with the molecular weights of the compounds.

The target solubility of the compounds is 25 to 50 g/L for suitable concentration of a catalytic treatment in an epi-pen with volume of 0.3 ml for the catalyst to reach 1/10 of an estimated deadly cyanide concentration.

Typical Procedure: The solubility of Na[Mo$_2$O$_2$S$_4$(met)] was first estimated based on experience during compound synthesis. A solution with concentration of exactly 0.2 mM was prepared and the molar absorptivity coefficients determined. Then a saturated solution was prepared in 10 mL water and the solution agitated overnight. The undissolved compound was centrifuged and 0.1 ml of the clear supernatant withdrawn and diluted to 50 ml or 100 ml in a volumetric flask to achieve absorbance of 1.0 a.u. or less. The absorbance of this solution was measured at 303 nm. The concentration was calculated based on the known molar absorptivity coefficient in mol/L, and converted to g/L by multiplying with the molecular weight.

TABLE 5

The table shows measured aqueous solubility of several complexes.

| Nr | Complex | Calc. Concentration [complex]$_{(aq)}$ (M) | Water Solubility, g/L |
|---|---|---|---|
| 1 | (Et$_4$N)$_2$[Mo$_2$O$_2$S$_8$] | $1.3 \times 10^{-3}$ | 0.5 |
| 2 | Mo$_2$O$_2$S$_4$(DMF)$_3$ | $6.2 \times 10^{-3}$ | 3.5 |
| 3 | Na[Mo$_2$O$_2$S$_4$(met)] | 0.049 | 25.0 |
| 4 | Na[Mo$_2$O$_2$S$_4$(leu)] | 0.120 | 60.0 |
| 5 | K$_2$[Mo$_2$O$_2$S$_2$(cys)$_2$] | 0.204 | 136.0 |

Example 7

Toxicity Studies in Mice.

Studies of the toxicity of three compounds in mice were undertaken. Compounds shown in entries 1,2 and 7 in Table 6 (compound 1, 2 and 7) were chosen since the first two were most likely to show a biological response, and then the third compound could be given ten times the dose value of compound 1 quantity based on toxicity results in cells. Compound 1 does not have sufficient solubility to reach our target molar concentration, so compound 2 was also employed. Single dose at maximum solubility for compounds 1 and 2 resulted in no observable biological responses.

TABLE 6

Toxicity studies in mice. Single dose administered at maximum solubility concentration of compound in buffer. Dose volume was 7.5 μL/Kg and three mice used per group. Concentration calculated assuming volume of blood is 2 ml in mice.

| Compound no. | Conc., g/L | Mouse | Calc. Concentration [complex]$_{(aq)}$ (μM) | Biological Response |
|---|---|---|---|---|
| 1 (Et$_4$N)$_2$[Mo$_2$O$_2$S$_8$] | 0.5 | 1 | 51.0 | no |
|  |  | 2 | 45.0 | no |
|  |  | 3 | 47.5 | no |
| 2 Mo$_2$O$_2$S$_4$(DMF)$_3$ | 1 | 1 | 130.0 | no |
|  |  | 2 | 122.0 | no |
|  |  | 3 | 118.0 | no |
| 7 Na$_2$[Mo$_2$O$_2$S$_2$(cys)$_2$] | 3.5 | 1 | 413.0 | no |
|  |  | 2 | 479.0 | no |
|  |  | 3 | 477.0 | no |

These studies show both compounds appear non-toxic in mice when given a single dose of the compounds showing the largest toxicity of the panel screened in vitro. Calculated (estimated volume) concentration shows the doses are within biologically relevant concentrations for the purpose of catalytic removal of cyanide, even the least soluble compound.

Protocol: Three mice per group, C57bl/6, male eight weeks old, were chosen for the studies. The mice were housed and monitored for one week before the experiment. Stock solutions of the compounds to be studied were prepared in dPBS buffer at the concentrations given in Table 4 on the day of study. Dose volume was 7.5 ml/Kg. The concentration of the solutions was verified by absorbance measurement. Each mouse was weighed and the total injection volume of the stock solution calculated based on the weight. Ex: A mouse that weighs 20.2 g was injected with 151.2 μL of the stock solution. The mice were observed for four hours immediately after injection, and then then next day. Their weight was monitored as well. No weight changes or biological responses were observed.

The invention claimed is:

1. A molybdenum compound according to the following formula:

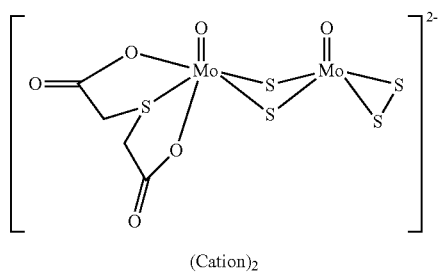

(Cation)$_2$

2. The compound according to claim 1, wherein the cation is selected from the group consisting of sodium, potassium, and R$_4$N, and, wherein R is selected from hydrogen, methyl, ethyl, propyl, Butyl, meglumine, glucosamine, ethanolamine, diethanolamine, triethanolamine (TEA), tromethamine (TRIS), N-methylaminoethanol, or N,N-dimethylaminoethanol.

3. A method of treating cyanide poisoning in a mammal, said method comprising administering a therapeutically effective amount of the compound of claim 1 to a mammal.

4. A method of treating cyanide poisoning in a mammal, said method comprising administering a therapeutically effective amount of a composition comprising a molybdenum compound according to the following formula:

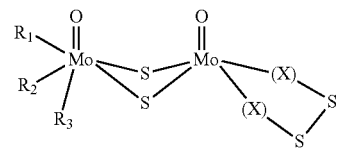

Wherein

X is S or a bond; and

R$_1$, R$_2$, and R$_3$ independently or together are one or more of the ligands selected from: a mono- or disaccharide having 3 to 12 carbon atoms, a natural amino acid, a primary, secondary, or tertiary amine, substituted with an alkyl having 1 to 5 carbon atoms, a mono- or di-carboxylic acid having 1 to 5 carbon atoms, which may be substituted with O, S, CH$_3$S— or N, a thiocarboxylic or thiodicarboxylic acid having 1 to 5 carbon atoms, a primary, secondary or tertiary amide having 1 to 5 carbon atoms, wherein the side chains attached to the nitrogen are an alkyl having 1 to 5 carbon atoms, EDTA, cyanide, thiocyanate (SCN$^-$), sulfite, disulfide or tetrasulfide, and wherein R$_3$ may be an electron pair.

5. The method according to claim 4, wherein the molybdenum compound has the formula:

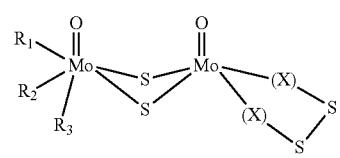

wherein X is S or a bond; and wherein R$_1$, R$_2$, and R$_3$ independently or taken together are one or more of the ligands selected from methionine, cysteine, threonine, serine, glutamate, malate, oxalate, methylsulfenyl succinate, mercapto succinate, dimethylformamide (DMF), cyanide, thiocyanate, thiosulfate, sulfite, disulfide or tetrasulfide, acetate, thiodiacetic acid, ammonium or diethylamine; and wherein R$_3$ may be an electron pair.

6. The method according to claim 5, wherein X is a bond.

7. The method according to claim 6, wherein the molybdenum compound has the formula:

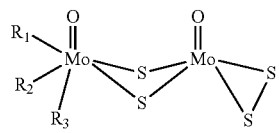

wherein R$_1$, R$_2$, and R$_3$ independently or taken together are one or more of the ligands selected from: methionine, cysteine, threonine, serine, glutamate, malate, oxalate, methylsulfenyl succinate, mercapto succinate, dimethylformamide (DMF), cyanide, thiocyanate, thiosulfate, sulfite, disulfide or tetrasulfide, acetate, thiodiacetic acid, ammonium or diethylamine.

8. The method according to claim 7, wherein $R_1$, $R_2$, and $R_3$ taken together are ligands selected from: methionine, cysteine, threonine, serine, glutamate, malate, oxalate, methylsulfenyl succinate, mercapto succinate, dimethylformamide (DMF), cyanide, thiocyanate, thiosulfate, sulfite, disulfide or tetrasulfide, thiodiacetic acid, ammonium or diethylamine.

9. The method according to claim 5, wherein X is S.

10. The method according to claim 4, wherein the molybdenum compound is in the form of a pharmaceutically acceptable salt.

11. The method according to claim 10, wherein the molybdenum compound is in the form of a salt having a cation selected from the group consisting of sodium, potassium, and $R_4N$, wherein R is either hydrogen, methyl, ethyl, propyl, or Butyl, meglumine, glucosamine, ethanolamine, diethanolamine, triethanolamine (TEA), tromethamine (TRIS), N-methylaminoethanol, or N,N-dimethylaminoethanol.

12. The method according to claim 4, further comprising a sulfur source.

13. The method according to claim 12, wherein the sulfur source is selected from the group consisting of: sulfur, thiosulfate, ammonium sulphide, dithiothreitol (DTT), trithiothreitol, gluthathione, and dibenzyl trisulfide (DTS).

14. The method according to claim 13, wherein the sulfur source is a salt selected from the group consisting of sodium thiosulfate and potassium thiosulfate.

15. The method according to claim 4, wherein the molybdenum compound is administered at a dose between 0.5 and 50 mg per kg body weight.

16. The method according to claim 12, wherein the molybdenum compound is administered at a dose between 0.25 and 25 mg per kilo body weight in combination with a sulfur source at a dose between 10 and 250 mg per kilo body weight.

17. The method according to claim 4, wherein the composition is formulated in a solid form configured for dissolution prior to administration.

18. The method according to claim 4, wherein the composition is administered intramuscularly, nasally, intra-peritoneally or intravenously.

19. The method according to claim 4, wherein the mammal is human.

20. The method according to claim 4, further comprising pharmaceutically acceptable excipients, vehicles or other pharmaceutically acceptable adjuvants.

21. The method according to claim 20, further comprising one or more further pharmaceutically active substances.

22. A method of treating cyanide poisoning in a mammal, said method comprising administering a kit comprising the compound according to claim 1.

23. The method according to claim 22, wherein the kit is in the form of an epi-pen.

24. A process for preparing the molybdenum compound according to claim 1, comprising:

1) suspending a molybdenum compound having the following formula:

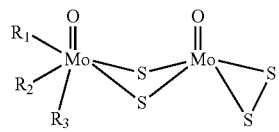

wherein $R_1$, $R_2$, and $R_3$ independently or together are one or more of the ligands selected from: a mono- or disaccharide having 3 to 12 carbon atoms, a natural amino acid, a primary, secondary, or tertiary amine, substituted with an alkyl having 1 to 5 carbon atoms, a mono- or di-carboxylic acid having 1 to 5 carbon atoms, which may be substituted with O, S, $CH_3S-$ or N, a thiocarboxylic having 1 to 5 carbon atoms, a primary, secondary or tertiary amide having 1 to 5 carbon atoms, wherein the side chains attached to the nitrogen are an alkyl having 1 to 5 carbon atoms, a complexing agent, EDTA, cyanide, thiocyanate ($SCN^-$), sulfite or tetrasulfide, and wherein $R_3$ may be an electron pair, in an inert solvent under an inert atmosphere;

2) adding 2,2'-thiodiacetic acid to the molybdenum compound in the presence of a base in a dry inert solvent under inert atmosphere and stirring the reaction mixture;

3) evaporating the solvent and precipitating; and 4) washing the precipitate with ethanol and ether, optionally, employing re-crystallisation.

25. The process of claim 24, wherein, in step 2), the reaction mixture is stirred at a temperature between 20° C. and 25° C.

26. The process according to claim 24, wherein, in the compound of step 1), $R_1$, $R_2$, and $R_3$ independently or taken together are one or more of the ligands selected from: methionine, cysteine, threonine, serine, glutamate, malate, oxalate, methylsulfenyl succinate, mercapto succinate, dimethylformamide (DMF), cyanide, thiocyanate, thiosulfate, sulfite or tetrasulfide, ammonium or diethylamine, and wherein $R_3$ may be an electron pair.

27. The process according to claim 24, wherein the base used in step 2) is selected from the group consisting of: NaOH, KOH, CsOH, $^tBuOK$, $^tBuONa$, NaOMe, KOMe, $^iPrONa$ $Na_2CO_3$, $K_2CO_3$, $Et_4NOH$, and $Bu_4NOH$.

28. The process according to claim 24, wherein the inert solvent in step 1) and 2) is a polar solvent selected from the group consisting of acetonitrile, water, DMF, acetone, THF, ethanol, methanol, DMSO (dimethyl sulfoxide), dioxane, DME (dimethoxyketone), glycol, and MEK (methylethylketone) or any combination thereof.

29. The process according to claim 24, wherein the inert atmosphere of step 1) and 2) is argon or nitrogen.

30. The process according to claim 24, wherein the reaction mixture is stirred for 15-60 minutes under step 2).

31. The process according to claim 24, wherein, in the compound of step 1), R1, R2 and R3 together are DMF.

* * * * *